(12) United States Patent
Parkins et al.

(10) Patent No.: US 7,740,104 B1
(45) Date of Patent: Jun. 22, 2010

(54) MULTIPLE RESONATOR ATTENUATING EARPLUG

(75) Inventors: John W. Parkins, Ithaca, NY (US); John R. MacGillivray, Ithaca, NY (US)

(73) Assignee: Red Tail Hawk Corporation, Ithaca, NY (US)

( * ) Notice: Subject to any disclaimer, the term of this patent is extended or adjusted under 35 U.S.C. 154(b) by 362 days.

(21) Appl. No.: 11/330,300

(22) Filed: Jan. 11, 2006

(51) Int. Cl.
*A61B 7/02* (2006.01)
(52) U.S. Cl. ............... 181/135; 181/128; 181/129; 181/130; 181/131; 181/133
(58) Field of Classification Search .......... 181/128, 181/129, 130, 131, 133, 134, 135, 132
See application file for complete search history.

(56) References Cited

U.S. PATENT DOCUMENTS

| | | | | | |
|---|---|---|---|---|---|
| 345,025 | A | * | 7/1886 | Blodgett | 181/136 |
| 2,437,490 | A | * | 3/1948 | Watson et. al. | 128/867 |
| 2,803,247 | A | * | 8/1957 | Zwislocki | 128/865 |
| 2,824,558 | A | * | 2/1958 | Michael et. al. | 128/865 |
| 3,047,089 | A | * | 7/1962 | Zwislocki | 181/135 |
| 3,131,241 | A | * | 4/1964 | Mendelson | 264/257 |
| 3,688,863 | A | * | 9/1972 | Johnson | 181/135 |
| 3,866,001 | A | * | 2/1975 | Kleinschmidt et al. | 181/285 |
| 4,311,206 | A | * | 1/1982 | Johnson | 181/135 |
| 4,413,198 | A | * | 11/1983 | Bost | 310/324 |
| 4,540,063 | A | * | 9/1985 | Ochi et al. | 181/135 |
| 4,556,122 | A | * | 12/1985 | Goode | 181/136 |
| 4,562,901 | A | * | 1/1986 | Junger et al. | 181/285 |
| 4,811,402 | A | * | 3/1989 | Ward | 381/322 |
| 4,944,362 | A | * | 7/1990 | Motsinger et al. | 181/213 |
| 5,261,006 | A | * | 11/1993 | Nieuwendijk et al. | 381/353 |
| 5,832,094 | A | * | 11/1998 | Le Her | 381/328 |
| 6,068,079 | A | * | 5/2000 | Hamery et al. | 181/135 |
| 6,164,409 | A | * | 12/2000 | Berger | 181/135 |
| 6,304,663 | B1 | * | 10/2001 | Claes et al. | 381/322 |
| 6,310,961 | B1 | * | 10/2001 | Oliveira et al. | 381/328 |
| 6,393,130 | B1 | * | 5/2002 | Stonikas et al. | 381/322 |
| 6,595,317 | B1 | * | 7/2003 | Widmer et al. | 181/135 |
| 6,691,822 | B2 | * | 2/2004 | Meussen et al. | 181/135 |
| 6,766,878 | B2 | * | 7/2004 | Widmer et al. | 181/135 |
| 6,827,178 | B2 | * | 12/2004 | Widmer et al. | 181/135 |
| 6,863,151 | B2 | * | 3/2005 | Widmer et al. | 181/129 |
| 6,898,289 | B2 | * | 5/2005 | Vanderveen et al. | 381/71.4 |
| 7,014,010 | B2 | * | 3/2006 | Widmer | 181/130 |
| 7,025,061 | B2 | * | 4/2006 | Haussmann | 128/864 |
| 7,089,901 | B2 | * | 8/2006 | Kino et al. | 123/184.57 |

(Continued)

*Primary Examiner*—Elvin G Enad
*Assistant Examiner*—Forrest M Phillips
(74) *Attorney, Agent, or Firm*—Brown & Michaels, PC

(57) ABSTRACT

A non-vented shell earplug for insertion into the ear canal has multiple chambers configured as coupled acoustic resonators. Each chamber is provided with an acoustic element having inertia and resistance coupling the chamber to its neighbor to form multiple resonant chambers. The dimensions of the individual acoustic elements set the frequency response of the earplug, and determine the attenuation characteristics of the resonators. Unlike the single chamber resonator of the prior art, the multiple-resonator earplug provides attenuation in both low and high frequency segments of the noise spectrum.

Additionally, the present invention teaches placing loudspeaker and/or sound sensing transducer for sound communication purposes and active noise control within the earplug, with their sound field patterns directed into a chamber for coupling to the ear canal. The use of multiple resonators enhances the high frequency communications response of the earplug.

17 Claims, 3 Drawing Sheets

U.S. PATENT DOCUMENTS

| | | | |
|---|---|---|---|
| 7,117,974 B2* | 10/2006 | Moenssen et al. | 181/277 |
| 7,185,655 B1* | 3/2007 | Redon | 128/864 |
| 7,185,734 B2* | 3/2007 | Widmer et al. | 181/135 |
| 7,240,765 B2* | 7/2007 | Berg et al. | 181/135 |
| 7,319,399 B2* | 1/2008 | Berg | 340/573.1 |
| 7,350,496 B2* | 4/2008 | Nakayama et al. | 123/184.57 |
| 7,407,035 B2* | 8/2008 | Stinauer et al. | 181/135 |
| 2002/0179365 A1* | 12/2002 | Meussen et al. | 181/135 |
| 2003/0051939 A1* | 3/2003 | Werblud | 181/131 |
| 2004/0026163 A1* | 2/2004 | Widmer et al. | 181/130 |
| 2004/0069560 A1* | 4/2004 | Widmer | 181/135 |
| 2005/0205354 A1* | 9/2005 | Goenka et al. | 181/277 |
| 2005/0252716 A1* | 11/2005 | Moenssen et al. | 181/277 |
| 2005/0274568 A1* | 12/2005 | Falco et al. | 181/135 |
| 2006/0042865 A1* | 3/2006 | Berg et al. | 181/135 |
| 2006/0042867 A1* | 3/2006 | Haussmann et al. | 181/135 |
| 2006/0042868 A1* | 3/2006 | Berg et al. | 181/135 |
| 2006/0137934 A1* | 6/2006 | Kurth | 181/135 |
| 2006/0162992 A1* | 7/2006 | Seville | 181/135 |

* cited by examiner

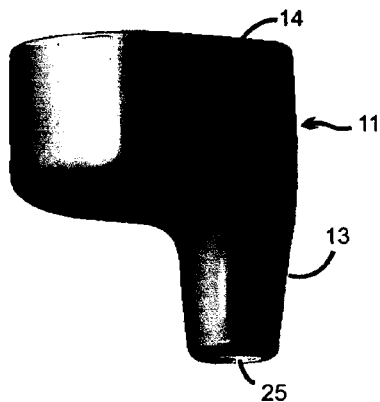
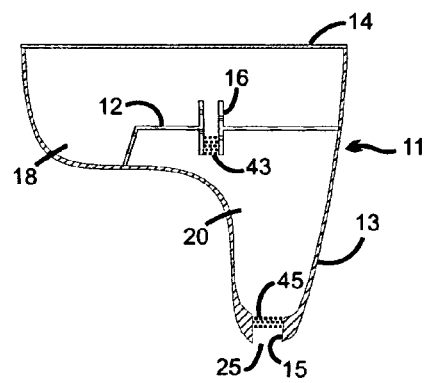
Fig. 1
Fig. 2
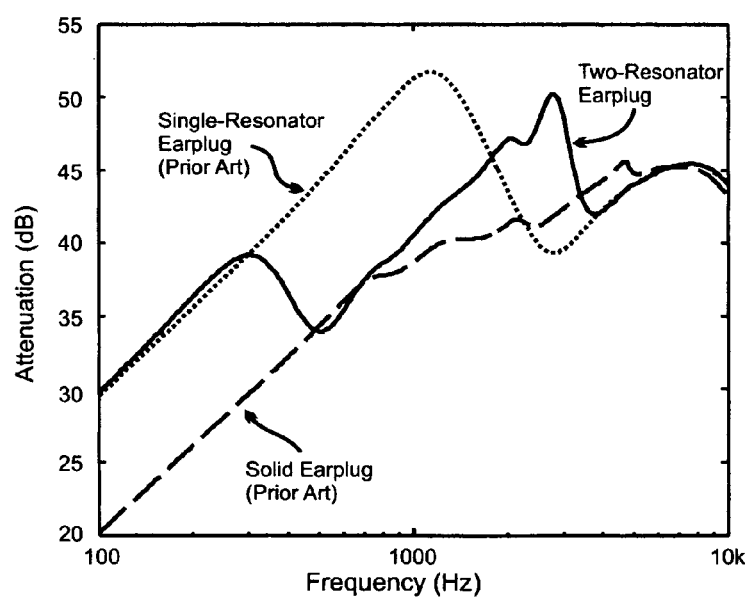
Fig. 3

MULTIPLE RESONATOR ATTENUATING EARPLUG

The U.S. Government has a paid-up license in this invention and the right in limited circumstances to require the patent owner to license others on reasonable terms as provided for by the terms of Contract N68335-03-C-0249 awarded by Dept of Defense.

BACKGROUND OF THE INVENTION

1. Field of the Invention

This invention relates to an earplug, and in particular to a non-vented, multiple-resonator, noise attenuating earplug for insertion into the ear canal.

2. Description Relative to the Prior Art

The deleterious effects on the hearing capability of a person subjected to a high amplitude ambient noise field are well known. Personnel such as miners, construction workers, aircraft maintainers, military tank operators, pilots, as well as many industrial employees are routinely and necessarily subjected to loud noise environments while performing their duties. Preventing ambient sound from entering the ear canal protects users from excessive ambient noise that causes hearing damage. In addition, attenuating ambient noise is beneficial in communications systems because higher speech intelligibility results.

When an earplug is inserted into an ear canal, ambient sound is transmitted into the canal through movement of the earplug, through air leaks around the earplug, by sound impinging on the body and by traveling through skin tissue and bone into the canal, as well as by sound transmission through the earplug itself. Solid earplugs constructed of polymeric foam, wax, rubber, acrylic are currently available, and have no internal resonators. The attenuation of a well-sealed solid earplug generally increases monotonically as a function of rising frequency.

U.S. Pat. No. 3,047,089, issued to J. J. Zwislocki, discloses a non-vented passive earplug having a single internal resonator. A sound chamber along with its sound opening into the ear canal form an acoustic resonating system, known as a Helmholtz resonator. The resonant frequency, $F_0$, of such a resonator is determined by the following formula:

$$F_0 = 1/(2\pi \sqrt{(M_1 C_1)})$$

where $M_1$ is the acoustic inertance at the sound opening and $C_1$ is the compliance of the chamber volume. As an example, for a chamber volume of 2.5 cc with a compliance of $1.76 \times 10^{-6}$ cm$^4$ s$^2$/g and the acoustic inertance is 0.01 g/cm$^4$; the resonance frequency is 1200 Hz. Above the resonance frequency, the acoustic impedance at the sound opening is relatively high, and the earplug attenuation matches that of a solid earplug. Below resonance, the impedance is relatively small, and the chamber of the earplug increases the occluded ear canal volume. This results in enhanced attenuation at frequencies below resonance. The improvement in the attenuation, in decibels (dB), is calculated from $$I = 20 \log((C_1 + C_c)/C_c)$$

where $C_c$ is the acoustic compliance of the occluded ear canal, which is approximately $8.60 \times 10^{-7}$ cm$^4$ s$^2$ when using an earplug. Therefore, in this example the improved attenuation below resonance is approximately 10 dB. The resonance of the system is primarily damped by viscous losses associated with movement of air through the sound opening. A problem with the single-chamber earplug is its limited high-frequency attenuation performance. Also when a loudspeaker, or other sound transmitting means is used with the earplug to provide communications for the user, the sound pressure level developed using the loudspeaker is significantly reduced compared to a solid earplug also having an attached loudspeaker.

U.S. Pat. No. 2,347,490, issued to Watson et al, discloses an earplug made of flexible resilient material having two chambers separated by a partition containing a cotton-packed cylindrical insert having a minute hole in its endplate to allow static pressure equalization between the chambers. Watson et al do not disclose chambers having the structure of multiple acoustic resonators because the chamber coupled to the ear canal does not employ an inertial element, and accordingly, the disclosed earplug does not exhibit the attenuation characteristic of multiple acoustic resonance.

U.S. Pat. No. 5,832,094, issued to Le Her discloses an earplug with an acoustic valve. The earplug disclosed by Le Her is vented, in that there is an acoustic path provided through the earplug to the ear canal under normal operating conditions. The invention of Le Her selectively transmits ambient sound through the earplug and into the ear canal at all times. This sound transmission increases the unwanted sound level in the ear canal and diminishes the hearing protection function of the earplug.

SUMMARY OF THE INVENTION

A non-vented shell earplug for insertion into the ear canal has multiple chambers configured as coupled acoustic resonators. Each chamber is provided with an acoustic element having inertia and resistance coupling the chamber to its neighbor to form multiple resonant chambers. The dimensions of the individual acoustic elements set the frequency response of the earplug, and determine the attenuation characteristics of the resonators. Unlike the single chamber resonator of the prior art, the multiple-resonator earplug provides attenuation in both low and high frequency segments of the noise spectrum.

Additionally, the present invention teaches placing loudspeaker and/or sound sensing transducer for sound communication purposes and active noise control within the earplug, with their sound field patterns directed into a chamber for coupling to the ear canal. The use of multiple resonators enhances the high frequency communications response of the earplug.

BRIEF DESCRIPTION OF THE DRAWINGS

The invention will be described with respect to the figures, of which:

FIG. 1 is a three-dimensional drawing of the earplug according to the present invention, FIG. 2 is a cross-sectional schematic drawing of an embodiment of the earplug according to the present invention, FIG. 3 is graph comparing the sound attenuation performance of earplugs of the prior art and an earplug according to the present invention.

DESCRIPTION OF THE PREFERRED EMBODIMENTS

Figure 4:
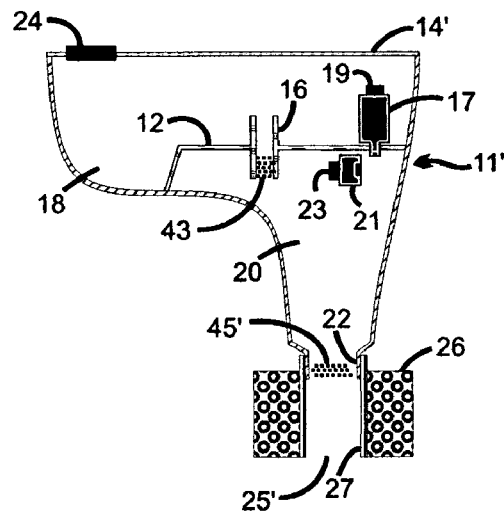
FIG. 4 is a drawing showing several modifications to the earplug of FIG. 2.

Referring to FIG. 1, an earshell, 11, is preferably fabricated from plastic, such as acrylic, with the earshell, 11, having adequate rigidity and wall thickness to impede appreciable sound transmission into its interior. A faceplate, 14, attaches to the earshell 11. The earshell, 11, is designed to fit the concha and canal of the wearer, much like an in-the-ear hearing aid, and is provided with an end, 13, designed to form a generally airtight seal when inserted in the ear canal. The earshell, 11, is non-vented having no openings to its interior except for a sound opening, 25, at the end 13, which provides the acoustic connection between the interior of the earshell 11, and the ear canal of the wearer.

A preferred embodiment of the multiple-resonator earplug configured as a two-chamber earplug is seen in schematic cross section in FIG. 2. A bulkhead, 12, separates the interior of the earshell, 11, into two chambers, 18, and 20. A tube, 16, serves as an acoustic port between the chamber, 18, and the chamber, 20. Tubes have properties of both acoustic inertance and acoustic resistance. The inertance is due to the entrained mass of air within the tube, while the resistance is due to thermo-viscous damping at the inner surface of the tube. The acoustic resistance of the tube, 16, is increased using acoustic damper, 43, within tube 16. Acoustic dampers are typically made of acoustic foam or wire mesh. At the end, 13, a tube, 15, couples the sound opening, 25, to the chamber 20. The chamber, 20, should have a volume of no greater than 2.0 cc if attenuation at high frequencies is desired. An acoustic damper, 45, increases the acoustic resistance of tube 15. It will be appreciated that chamber 18, and chamber 20, the tube 16 and the tube, 15, and the acoustic resistance 43, 45 are elements of coupled acoustic resonators. In this example, the tube, 16, is 9.7 mm long, with a diameter of 1.0 mm, and the tube, 15, is 2.0 mm long with a diameter of 1.76 mm. The chamber, 18, has a volume of 2.0 cc, and the chamber, 20, has a volume of 0.5 cc. The inertance of the tube, 16, is 0.15 gm/cm$^4$, acoustic resistance, 43, is 200 gm cm$^{-4}$ sec$^{-1}$, and tube, 15, has an inertance of 0.01 gm/cm$^4$, and the acoustic damper, 45, has acoustic resistance of 50 gm cm$^{-4}$ sec$^{-1}$. The chamber, 18, has a compliance of $1.41 \times 10^{-6}$ cm$^4$ sec$^2$/g, and the chamber, 20, has a compliance of $0.35 \times 10^{-6}$ cm$^4$ sec$^2$/g. The magnitudes of these physical parameters are set by the components' dimensions, the density of air, and the speed of sound, and determine the resonant frequencies of the resonators in accordance with the formula cited above. The acoustic resistances 43, 45 are empirically determined by the resistance materials incorporated into the tube, 16, and tube, 15.

Referring to FIG. 3 which graphs the attenuation arising from, (1), the practice of the invention shown in FIG. 2, and for comparison, (2), the attenuation of a solid earplug, and, (3), of a resonator earplug having only one resonator. For the two chamber earplug of the invention, at low frequencies the inertance, 0.15 gm/cm$^4$, of the tube, 16, exhibits a low impedance and effectively connects the chamber, 18, and the chamber, 20, so the earplug has a total chamber volume of 2.5 cc. The compliance of chamber 18, which has a value of $1.41 \times 10^{-6}$ cm$^4$ sec$^2$/g, and the inertance of the tube, 16, i.e., 0.15 g/cm$^4$, comprise a resonator having a resonant frequency of 346 Hz. Therefore, the attenuation of the earplug of the invention, and that of a single-resonator earplug of the same chamber size and same sound opening characteristics track each other, and show a 10 dB improvement over the solid earplug.

In the region of resonance, i.e. 346 Hz, the attenuation of the two-resonator earplug rolls off to the level of that of a solid earplug, until about 1100 Hz, where its attenuation begins to rise again. From about 1100 Hz, the two-resonator earplug has a steadily increasing attenuation, greater than that either exhibited by the single-resonator earplug or the solid earplug, until it starts to fall off again at about 2700 Hz. This frequency is the resonant frequency of the resonator formed by chamber, 20, and tube, 15. The magnitude of the peak in the attenuation at 2700 Hz is controlled by the acoustic damper 45. The magnitude of the peak in attenuation at 346 Hz is controlled by the acoustic damper 43. The impedance of tube, 16, being sufficiently high in this frequency range as to essentially isolate the volume of the chamber, 18, from influencing the overall attenuation. Hence, the multiple-resonator earplug not only provides attenuation in the low frequency region of the noise spectrum, but provides enhanced noise attenuation and hearing protection in the 2000 Hz to 3000 Hz range, where the ear is more prone to hearing damage compared to the region below 1000 Hz. This boost in high frequency noise attenuation is also advantageous in reducing the noise level in the band critical for intelligible speech communication, as is described below.

A modification of the invention of FIG. 2, useful further in improving speech communication with a wearer of the earplug of FIG. 2 is included in FIG. 4. For improved communications, a sound generating transducer, 17, and a sound sensing transducer (such as a microphone), 21, are mounted on the bulkhead, 12. The sound sensing transducer, 21, may be used to implement an active noise control system, or may be used for sensing sound in the ear canal. In practice, either one or both sound transducers, 17, or 21, may be included in given earshell, 11', depending upon the intended application for the earplug. (In the drawings different but related elements are identified by the same reference character, albeit that the different elements are distinguished by primes.) In either case, the sound field patterns of the transducers, 17, 21 may be but are not necessarily directed into the chamber, 20, having the sound opening, 25', that communicates with the ear canal of the wearer.

Figure 5:
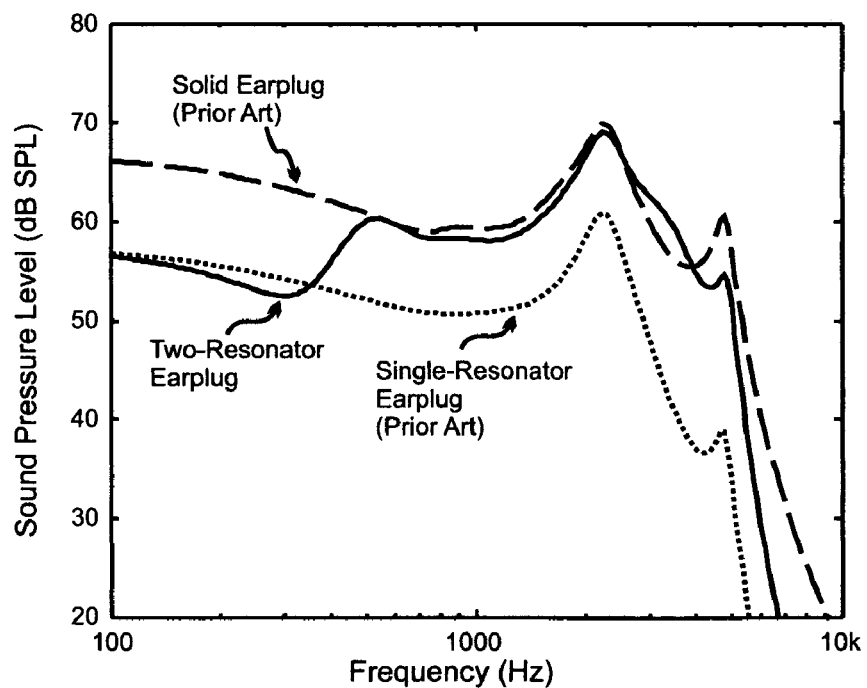
FIG. 5 is a graph comparing the sound communication characteristics of earplugs of the prior art and the earplug in according to the present invention.

The effectiveness of this modification may be seen by referring to FIG. 5, wherein the sound pressure level at the eardrum is compared for that of, (1), a sound generating transducer mounted as described above, (2), for a speaker driving the free end of a solid earplug, and (3), for a speaker mounted to drive a single-resonator earplug having a volume equal to the total volume of the two chambers of the two-resonator earplug earshell, 11'. For the same earplug parameter values used in the above example discussing attenuation, at low frequencies it is seen that the two-resonator earplug of the invention and the single-resonator earplug result in the same performance up to the resonance frequency of 346 Hz. This is to be expected due to the identical compliances of the two earplugs over this range, as explained above. However, above this resonance frequency, the two-resonator earplug, 11', exhibits a 10 dB increase in signal level, due to the decreased volume being driven by the sound generating transducer, 17. This improvement in efficiency of the two-resonator earplug holds over the entire frequency range essential for speech communication. It will also be noted that the sound sensing transducer, 21, when mounted in a corresponding manner to interface with the chamber, 20, will exhibit the same improvement relative to the single-resonator earplug. Electrical connections to transfer signals to or from the transducers, 17, 21 may be through connectors, 19, 23, having wire connections to external circuits, or to wireless transmission devices attached to earshell, 11'.

FIG. 4 further illustrates a second modification to the earplug of the invention, wherein a pressure equalization valve, 24, communicating with the interior of the earshell, 11', is mounted through faceplate, 14'. Under normal conditions, the valve, 24, is completely closed forming an airtight seal preventing transmission of any sound through the valve, 24. When a preset static pressure differential between the interior of the earshell, 11', and the ambient air is exceeded, the valve, 24, opens to equalize the pressure. The valve, 24, is preset to open if the pressure differential is high enough to cause discomfort in the ear canal of the earplug wearer.

Another modification of the earshell, 11', is that the end, 13, of FIG. 2 is converted into a nipple, 22, configured to accept a shaped foam or other resilient material eartip, 26, mounted on a tube, 27, insertable onto the nipple, 22. The eartip, 26, provides a more comfortable and more air tight connection to the ear canal, and, it and tube, 27, may be removed from the nipple, 22, for replacement, by use of reasonable force. The air within the cylindrical nipple, 22, and tube, 27, provide an inertance. The sound opening, 25', is now at the end of the tube, 27.

Figure 6:
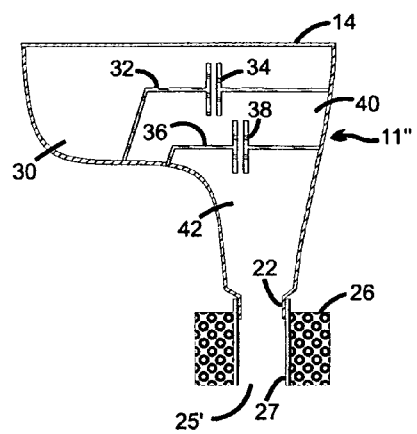
FIG. 6 is a drawing of a second embodiment of the earplug of the invention having multiple sound resonators.

A third embodiment of the invention of the multiple-resonator earplug of the invention is illustrated in FIG. 6. An earshell, 11", may be externally configured the same as the earshell, 11', of FIG. 4; however, the interior of earshell, 11", is divided into three resonant chambers. A partition, 32, forms a first chamber, 30, in the interior of earshell, 11", a partition, 36, divides the remaining volume into two chambers, 40, 42. A tube, 34, connecting chambers 30, 40, a tube, 38, connecting chambers 40, 42, and tube, 27, along with nipple 22, provide the inertance for interacting with chambers 30, 40, 42 to form Helmholtz resonators. In this example, tubes 34 and 38 do not employ acoustic dampers. However, acoustic damping is provided by thermo-viscous damping at the inner surface of the tubes. The specific dimensions of the chambers 30, 40, 42, the tubes, 34, 38, 27, the nipple, 22, and any required acoustic resistances are parameters to be determined by the attenuation and frequency specifications of the multiple chamber earplug design.

Figure 7:
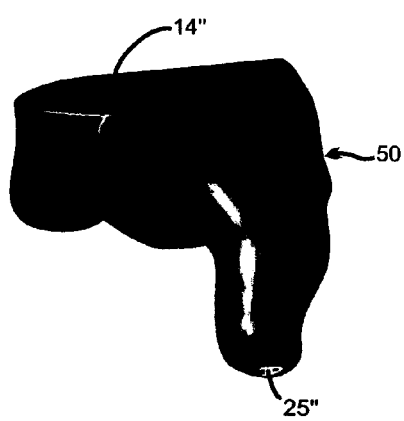
FIG. 7 is a drawing of the earplug of the invention configured with a custom-molded earshell.

Referring to FIG. 7, the earplug of the invention may be implemented with an earshell, 50, custom molded to the contours of the ear of the wearer. The interior of the earshell, 50, is configured for the practice of the invention as disclosed in the embodiments and modifications above.

Figure 8:
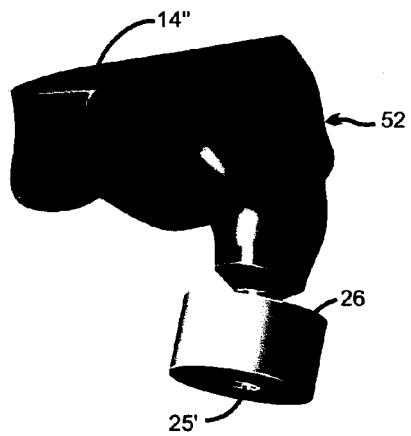
FIG. 8 is a drawing of the earplug of the invention configured with a custom-molded earshell with a removable eartip.

Referring to FIG. 8, the earplug of the invention may be implemented with an earshell, 52, custom molded to the contours of the ear of the wearer where the removable eartip, 26, shown in FIG. 6, is used to achieve a better acoustic seal between the earshell and ear canal. The interior of the earshell, 52, is configured for the practice of the invention as disclosed in the embodiments and modifications above.

The invention has been described in detail with particular reference to preferred embodiments thereof, but it will be understood that variations and modifications can be effected within the scope of the invention.

What is claimed is:

1. A nonvented earplug having a sound hole for coupling said earplug to a user's ear canal, said earplug comprising:
    a) an enclosure encompassing a volume, said enclosure comprising an earshell having a faceplate facing away from a user when the earplug is worn in a user's ear canal, and an end opposite the faceplate, shaped to form a generally airtight seal when inserted in the ear canal, the earshell having no openings to the volume except for a sound hole at the end which provides an acoustic connection between the volume and the ear canal of the wearer;
    b) said volume subdivided by at least one bulkhead into a plurality of chambers,
    c) a plurality of acoustic inertance elements, wherein each one of said plurality of chambers is connected to at least one other of said plurality of chambers by an inertance element of said plurality of acoustic inertance elements passing through a bulkhead, whereby said plurality of chambers and said plurality of inertance elements form a plurality of acoustic resonators, and
    d) one of said plurality of acoustic resonators is coupled to said sound hole.

2. The earplug of claim 1 wherein said enclosure is made of a substantially rigid plastic.

3. The earplug of claim 1 wherein said plurality of acoustic resonators includes acoustic resistive damping.

4. The earplug of claim 1 wherein each one of said plurality of acoustic resonators is acoustically coupled to at least another one of said acoustic resonators.

5. The earplug of claim 1 wherein said enclosure contains a loudspeaker having its sound pattern directed into one of said plurality of acoustic resonators.

6. The earplug of claim 5 wherein said loudspeaker includes means for electrically driving said loudspeaker from outside of said earplug.

7. The earplug of claim 6 wherein said means for electrically driving said loudspeaker comprises wired connections to said loudspeaker.

8. The earplug of claim 6 wherein said means for electrically driving said loudspeaker comprises wireless means for electrically driving said loudspeaker.

9. The earplug of claim 1 wherein said enclosure contains a sound transducer having its sound pattern directed into one of said plurality of acoustic resonators.

10. The earplug of claim 9 wherein said sound transducer includes means for electrically providing signal from said sound transducer to outside of said earplug.

11. The earplug of claim 10 wherein said means for electrically providing signal from said sound transducer to outside said earplug comprises wired connections to said sound transducer.

12. The earplug of claim 10 wherein said means for electrically providing signal from said sound transducer to outside said earplug comprises wireless transmission means.

13. The earplug of claim 1 including a normally closed pressure equalization valve wherein excess pressure in said earplug causes said pressure equalization valve to open, whereby said excess pressure is vented.

14. The earplug of claim 1 wherein said sound hole further comprises a sound conductive tubular element having mounted thereon a removable soft foam sleeve, whereby comfortable contact and acoustic seal with said ear canal is enhanced during use of said earplug.

15. The earplug of claim 1 configured to custom fit the concha of a user's ear.

16. The earplug of claim 15 further comprising an eartip.

17. A method of attenuating noise by an earplug worn in a user's ear in a noisy environment, said method comprising the steps of:
    a) fabricating a nonvented plastic shell having a hollow volume therein, comprising an earshell having a faceplate facing away from a user when the earplug is worn in a user's ear canal, and an end opposite the faceplate, shaped to form a generally airtight seal when inserted in the ear canal, the earshell having no openings to the volume except for a sound hole at the end which provides an acoustic connection between the volume and the ear canal of the wearer;

b) dividing said volume into a plurality of separate acoustic resonators by at least one bulkhead,
c) connecting each of said plurality of resonators to at least one other of said plurality of resonators by an inertance element passing through a bulkhead,
d) coupling one of said plurality of separate acoustic resonators with a sound hole for coupling said earplug to said user's ear for attenuating said noise.

* * * * *